(12) United States Patent
Kana et al.

(10) Patent No.: US 9,161,841 B2
(45) Date of Patent: Oct. 20, 2015

(54) INTERBODY FUSION DEVICE AND ASSOCIATED METHODS

(71) Applicant: SpineSmith Partners, L.P., Austin, TX (US)

(72) Inventors: Richard J. Kana, Lexington, TX (US); Luis Duarte, San Angelo, TX (US); Mukund Gundanna, College Station, TX (US)

(73) Assignee: SpineSmith Partners, L.P., Austin, TX (US)

( * ) Notice: Subject to any disclaimer, the term of this patent is extended or adjusted under 35 U.S.C. 154(b) by 0 days.

(21) Appl. No.: 14/020,374

(22) Filed: Sep. 6, 2013

(65) Prior Publication Data

US 2014/0012384 A1    Jan. 9, 2014

Related U.S. Application Data

(63) Continuation-in-part of application No. 13/135,675, filed on Jul. 12, 2011, and a continuation-in-part of application No. 13/200,911, filed on Oct. 4, 2011, now Pat. No. 8,597,353.

(60) Provisional application No. 61/697,795, filed on Sep. 6, 2012.

(51) Int. Cl.
*A61F 2/44* (2006.01)
*A61B 17/80* (2006.01)
(Continued)

(52) U.S. Cl.
CPC ............ *A61F 2/4465* (2013.01); *A61F 2/30744* (2013.01); *A61F 2/4455* (2013.01); *A61L 27/18* (2013.01); *A61B 17/8033* (2013.01);
(Continued)

(58) Field of Classification Search
CPC . A61F 2002/4475; A61F 2/4455; A61F 2/44; A61F 2002/30131; A61B 17/8033; A61B 17/8038; A61B 17/8042
USPC ............................................ 623/17.11–17.16
See application file for complete search history.

(56) References Cited

U.S. PATENT DOCUMENTS

5,980,523 A * 11/1999 Jackson .......................... 606/252
6,306,139 B1 * 10/2001 Fuentes ........................... 606/70
(Continued)

*Primary Examiner* — Eduardo C Robert
*Assistant Examiner* — Julianna N Harvey
(74) *Attorney, Agent, or Firm* — Winstead PC (57) ABSTRACT

A method and apparatus is provided for use in spinal fusion procedures. An interbody fusion device has a first piece that is a load bearing device designed to bear the axial loading from the end plates of adjacent vertebrae. A second piece of the interbody fusion device is a retention component whose primary functions are to prevent migration of the load bearing device and loss or migration of graft material from within the load bearing device. A secondary function of the retention component is to address fixation of fasteners when the surgeon is confronted with a challenging access to adequate boney structures due to excessive curvature/angulation of the vertebrae column, minimal invasive surgery techniques, danger to surrounding vascular or neurological tissues, poor bone quality, or similar surgical complications. A tertiary function of the retention component is to provide better alignment and stabilization of misaligned vertebrae when spondylolisthesis is a significant factor. One or more fasteners secure the retention component to each of the vertebrae above and below the load bearing device. The fasteners cause the end plates of the vertebrae to compress the end plates to the load bearing device to facilitate proper fusion.

6 Claims, 9 Drawing Sheets

(51) Int. Cl.
*A61F 2/30* (2006.01)
*A61L 27/18* (2006.01)
*A61F 2/28* (2006.01)

(52) U.S. Cl.
CPC . *A61F2002/2817* (2013.01); *A61F 2002/2835* (2013.01); *A61F 2002/3008* (2013.01); *A61F 2002/30131* (2013.01); *A61F 2002/30171* (2013.01); *A61F 2002/30331* (2013.01); *A61F 2002/30354* (2013.01); *A61F 2002/30504* (2013.01); *A61F 2002/30578* (2013.01); *A61F 2002/30607* (2013.01); *A61F 2002/30616* (2013.01); *A61F 2002/30774* (2013.01); *A61F 2002/30782* (2013.01); *A61F 2002/30904* (2013.01); *A61F 2002/4475* (2013.01); *A61F 2310/00011* (2013.01); *A61L 2430/38* (2013.01)

(56) References Cited

U.S. PATENT DOCUMENTS

| | | | |
|---|---|---|---|
| 6,413,259 B1 * | 7/2002 | Lyons et al. | 606/295 |
| 2004/0193269 A1 * | 9/2004 | Fraser et al. | 623/17.11 |
| 2004/0199254 A1 * | 10/2004 | Louis et al. | 623/17.11 |

* cited by examiner

INTERBODY FUSION DEVICE AND ASSOCIATED METHODS

CROSS-REFERENCES TO RELATED APPLICATIONS

This Application claims the benefit under 35 U.S.C. §119 (e) of U.S. Provisional Patent Application No. 61/697,795 filed Sep. 6, 2012, which is incorporated herein by reference in its entirety as if fully set forth herein. This Application is a continuation-in-part of application Ser. No. 13/135,675 filed Jul. 12, 2011 and is a continuation-in-part of application Ser. No. 13/200,911 filed Oct. 4, 2011, each of which is incorporated herein by reference in its entirety as if fully set forth herein.

FIELD OF THE INVENTION

This invention relates to the field of spinal fusion. In particular, this invention is drawn to spinal fusion devices and associated methods.

BACKGROUND OF THE INVENTION

The spine can be considered to be a series of movable segments made up of vertebrae and discs. Due to trauma, disease, and/or aging, the spine may be subject to degeneration. This degeneration may destabilize the spine and cause pain and/or nerve damage. Medical procedures are often required to either ease back pain, repair damage, or to prevent future damage.

One procedure that is often used to treat back pain or spinal damage is spinal fusion. Spinal fusion is a surgical technique used to combine two or more adjacent vertebrae. Supplemental bone tissue is used in conjunction with the patient's natural osteoblastic processes in a spinal fusion procedure. Spinal fusion is used primarily to eliminate back pain caused by the motion of the damaged vertebrae by immobilizing adjacent vertebrae. Conditions for which spinal fusion might be done include degenerative disc disease, treatment of a spinal tumor, a vertebral fracture, scoliosis, degeneration of the disc, spondylolisthesis, or any other condition that causes instability of the spine.

One problem with prior art spinal fusion techniques relates to device migration. For example, prior to complete bone fusion, a fusion device may migrate from the desired position. In examples where bone screws are used, the insertion and tightening of the bone screws tends to cause device migration. Another problem with typical prior art fusion techniques is that fusion devices, or associated plates or fasteners, protrude excessively from the spine, causing discomfort, damage, or danger to surrounding vascular or neurological tissues. A further problem with prior art fusion techniques also involves trajectories of screws that are used in the fusion process.

Yet another problem with the prior art fusion techniques is the difficulty with placing supplemental fixation (i.e., plates and screws) due to gross anatomy constraints, surgical approach, vasculature and neurologic tissues and structures, and variable bone quality of the vertebrae.

There is therefore a need for spinal fusion devices and related spinal fusion procedures that adequately treats degenerative disc disease and other spinal conditions, while providing improvements over the prior art.

SUMMARY OF THE INVENTION

An apparatus of the invention provides a spinal fusion device including a fusion bearing component configured to fit between two adjacent vertebrae, and a retention component configured to be secured to at least one of the adjacent vertebrae to prevent migration of the fusion bearing component, wherein the retention component has a minimalist profile that reduces the potential to cause discomfort, damage, or danger to surrounding vascular or neurological tissues.

One embodiment of an interbody fusion device includes a first piece configured to be placed between adjacent vertebrae, a second piece configured to at least partially fit within the first piece when the first piece is inserted between adjacent vertebrae, and one or more fastening devices for securing the second piece to at least one of the adjacent vertebrae.

Another embodiment of the invention provides a spinal fusion device including a fusion bearing component configured to fit between two adjacent vertebrae, a retention component configured to prevent migration of the fusion bearing component and loss or migration of bone forming matrix placed in the fusion bearing component to promote fusion, wherein the retention component has a minimalist profile that reduces the potential to cause discomfort, damage, or danger to surrounding vascular or neurological tissues, one or more fasteners coupled to the retention component to compress the two adjacent vertebrae to the fusion bearing component.

Another embodiment of the invention provides a method of fusing adjacent vertebrae including providing an interbody fusion device, inserting the interbody fusion device between two adjacent vertebrae, preparing the vertebral endplates for fusion, adding a bone forming matrix to promote fusion, providing a retention component configured to attach to the interbody fusion device, attaching the retention component to the interbody fusion device, and securing the retention component to at least one of the adjacent vertebrae.

Other features and advantages of the present invention will be apparent from the accompanying drawings and from the detailed description that follows below.

BRIEF DESCRIPTION OF THE DRAWINGS

The present invention is illustrated by way of example and not limitation in the figures of the accompanying drawings, in which like references indicate similar elements and in which:

FIG. 3 is an isometric diagram of the interbody fusion device shown in

FIG. 1 installed between the end plates of two adjacent vertebrae;

DETAILED DESCRIPTION OF EXEMPLARY EMBODIMENTS

The present invention relates to spinal fusion implants and related spinal fusion procedures for use in cervical and lumbar applications. One type of spinal fusion is interbody fusion. Typically, an interbody fusion procedure places a bone graft between the vertebrae in the area normally occupied by an intervertebral disc. In preparation for a spinal fusion procedure, the intervertebral disc is removed. A device, typically containing a bone promoting matrix, such as allograph bone, may be placed between the vertebra to maintain spine alignment and disc height. Fusion then occurs between the endplates of the vertebrae. In some examples, fusion is augmented by a process called fixation, meaning the placement of screws, rods and/or plates to stabilize the vertebra to facilitate bone fusion. The present invention provides an interbody fusion device that overcomes problems found in the prior art, such as the angles of the screws, rods and/or plates that are used to stablize the vertebra.

Generally, the present invention provides a two-piece interbody fusion device that may be used to perform anterior lumbar interbody fusion (ALIF). In one example, a first piece of the interbody fusion device is a U-shaped load bearing device that is designed to bear the axial loading from the end plates of adjacent vertebrae. A second piece of the interbody fusion device is a retention component, which may be attached to the U-shaped load bearing device, whose function is to prevent migration of the load bearing device and to prevent loss or migration of the bone forming matrix placed therein. One or more fasteners, such as bone screws secure the retention component to the vertebrae above and below the load bearing device. The fasteners cause the end plates of the vertebrae to compress the end plates to the load bearing device to facilitate proper fusion. If desired, the fasteners may include an anti-backout mechanism to prevent their migration.

Figure 1:
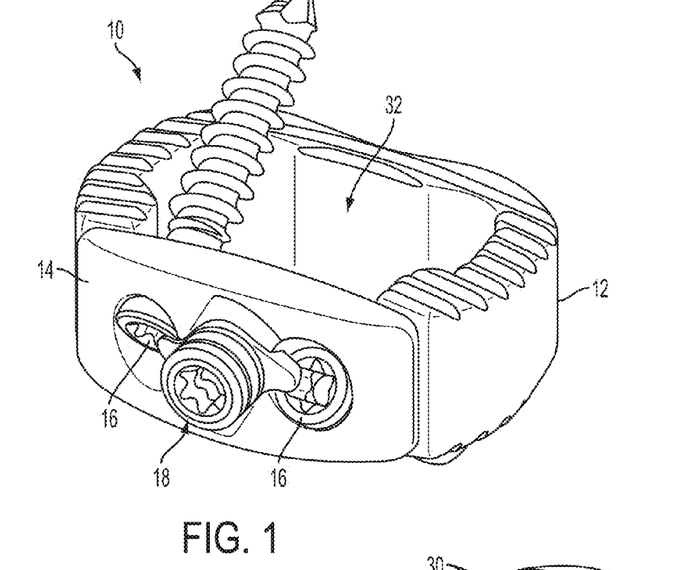
FIG. 1 is an isometric view of one example of an interbody fusion device in accordance with an embodiment of the invention.

FIG. 1 is an isometric view of one example of an interbody fusion device of the present invention. FIG. 1 shows an interbody fusion device 10. The interbody fusion device 10 includes a load bearing device 12, a retention component 14, two bone screws 16, and an anti-backout mechanism 18, each of which are described in more detail below. The interbody fusion device comprises a hollow region 32 which can be filled with a prepared material such as a bone forming matrix to help facilitate fusion of the vertebrae.

Figure 2:
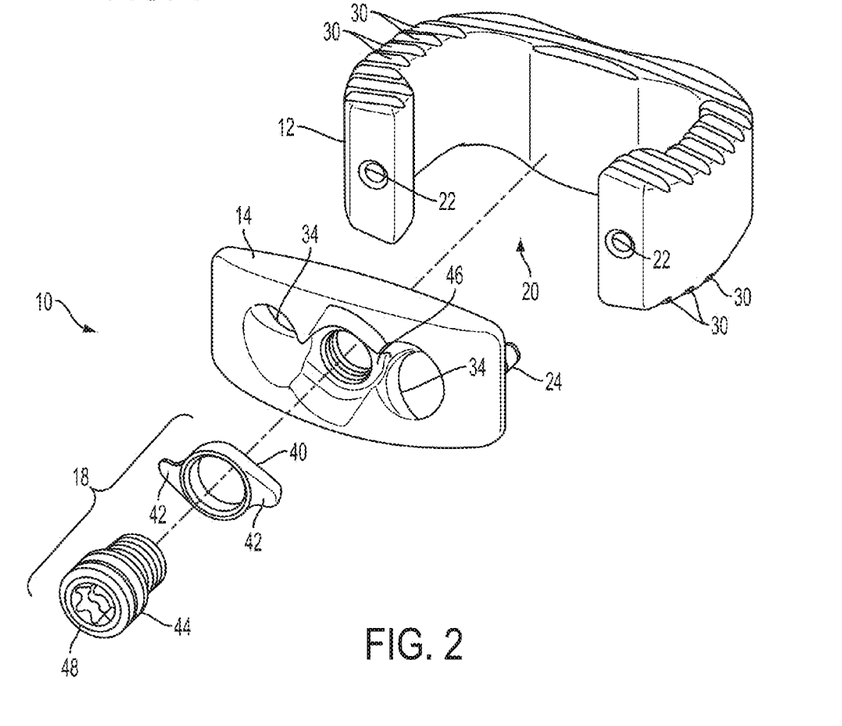
FIG. 2 is an exploded isometric diagram of the interbody fusion device shown in FIG. 1 without the bone screws in accordance with an embodiment of the invention.

FIG. 2 is an exploded view of the interbody fusion device 10, showing the load bearing device 12, the retention component 14, and the anti-backout mechanism 18 separately. The load bearing device 12 is a generally U-shaped device having an open end 20. The open end defines an opening that allows access to the vertebrae end plates when the load bearing device is installed. The leading edges of the load bearing device 12 include holes or openings 22, which are configured to receive pins 24 extending from the retention component 14. The pins 24 properly align the retention component 14 with the load bearing device 12 and hold the retention component 14 in a desired position, relative to the load bearing device 12.

The load bearing device 12 also includes a plurality of ridges 30 formed on the top and bottom ends of the device 12. The ridges 30 are angled and pointed in such a way that the ridges 30 help to hold the load bearing device 12 to the end plates of the vertebrae to reduce the chance of anterior migration of the implant. If desired, one or more openings (not shown) can be formed in the load bearing device 12 to facilitate the attachment of instrumentation devices.

FIG. 2 also illustrates the components of the anti-backout mechanism 18. The anti-backout mechanism 18 includes a locking plate 40. The plate 40 has two opposing protrusions 42 that extend outward from the plate 40. A set screw 44 is configured to extend through an opening formed in the plate 40, and thread into the retention component 14. A recess 46 is formed in the retention component 14 that is adapted to receive the locking plate 40. The set screw 44 includes a head 48 that will shear off when enough torque is applied by a driver. By shearing off the head 48, the surgeon will know that the set screw 44 is tight enough, and it will reduce the profile of the fusion device 10. The retention component 14, locking plate 40, and set screw 44 can be pre-assembled, such that a surgeon will have a single piece that is attached to the load bearing device 12. Once the bone screws are installed, the surgeon needs only to turn the set screw 44 with a driver to lock the bone screws in place. When the head 48 shears off, it will stay attached to the driver as the surgeon removes the driver from the patient. More details of the operation of the anti-backout mechanism 18 is described below. The set screw in this example includes a driver socket for receiving a driver, which may be used by a surgeon to tighten the set screw 44. Of course, any desired type of anti-backout device may also be used.

Figure 3:
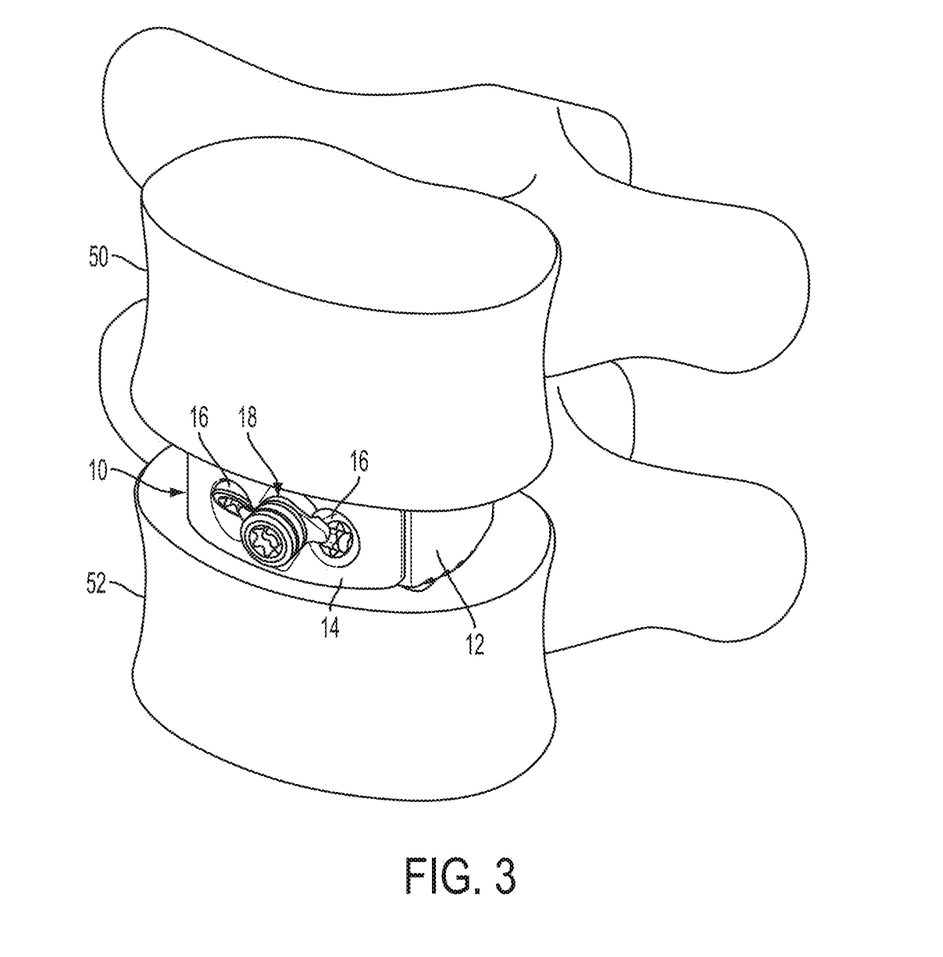

As described above, an interbody fusion device of the present invention is intended to be installed between the end plates of two adjacent vertebrae to facilitate the fusion of the vertebrae. FIG. 3 is an isometric diagram of the interbody fusion device 10 shown in FIG. 1 installed between the end plates of two adjacent vertebrae 50 and 52 to facilitate the fusion of the vertebrae 50 and 52. The interbody fusion device 10 provides load bearing support as well as the proper spacing between the vertebrae 50 and 52 while fusion of the vertebrae takes place. As described in more detail below, the interbody fusion device 10 is positioned between the end plates of the vertebrae 50 and 52 within the vertebral body in the area usually occupied by the intervertebral disc. For clarity, the disc annulus is not shown, so the position of the load supporting device 12 can be seen.

Following is an example of how an interbody fusion device of the present invention may be used in an ALIF spinal fusion procedure. As described above, a window is cut in the anterior side of the disc annulus to allow an interbody fusion device to be inserted. Next, the nucleus pulposus is cleaned out to provide room for the interbody fusion device. Next, a load bearing device 12 of the desired size (e.g., having a height to get the desired spacing between the vertebrae and surface area to maximize coverage of the endplates) is inserted between the end plates of the adjacent vertebrae using the appropriate instrumentation. Once the surgeon is satisfied that the load bearing device is in the desired position, the end plates can be prepared using the appropriate instruments (e.g., burrs, gouges, curettes, etc.). Next, the space between the endplates and within the load bearing device can be filled with a material that will help to facilitate fusion. Next, the retention component 14 is coupled to the load bearing device 12, while aligning the pegs 24 with the holes 22. Note that, because the height of the retention component is less than the height of the load bearing device, the retention component 14 can be put in place without interfering with the relative placement of the load bearing device 12 and the end plates of the adjacent vertebrae. Also, the retention component 14 is stress shielded and is not axial loaded by the vertebrae. Once the retention component is in place, the bone screws 16 can be installed through the openings 34 and into the vertebrae. As the bone screws 16 are tightened, the vertebrae will compress vertebral bodies 50 and 52 onto the load bearing member 12, which will help facilitate fusion. Also, since the bone screws 16 secure the retention component 14, and do not directly secure the load bearing device 12, the bone screws will not tend to cause the interbody fusion device 10 to migrate. Next, the anti-backout mechanism 18 is engaged to prevent the bone screws 16 from loosening. As is described in detail below, the surgeon can turn the set screw 44 with driver until the head 48 sheers off. The protrusions 42 of the locking plate 40 will then be positioned over the ends of the bone screws 16, preventing the screws 16 from backing out.

The interbody fusion device of the present invention can be made from any desired materials. In one example, the load bearing device is made from PEEK® (or a similar material), bone, metal, or any other structural substitute. If the components of the interbody fusion device are radio-lucent (such as with PEEK®), then doctors will be able to monitor the fusion process better with X-rays. If desired, one or more radio opaque markers can be embedded into the interbody fusion device, which will show up in an X-ray. Since the positions of the markers are known relative to the fusion device, a doctor can determine the position of the fusion device in an X-ray by viewing the positions of the markers.

An interbody fusion device of the present invention may be configured to any desired size or shape. In one example, load bearing devices can be provided in multiple thicknesses, allowing a surgeon to select a desired size (e.g., 8.0 mm, 10.0 mm, 12.0 mm, 14 mm, etc.). In the examples shown in the figures, the load bearing device has about 5° of lordosis. Of course any desired angle could be used.

Figure 4:
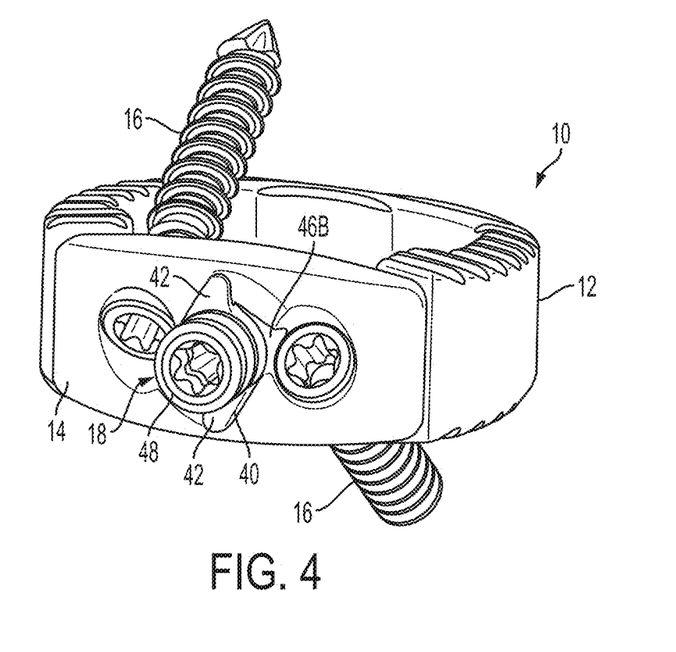
FIGS. 4-6 are isometric views illustrating the operation of a fusion device in accordance with an embodiment of the invention.
Figure 5:
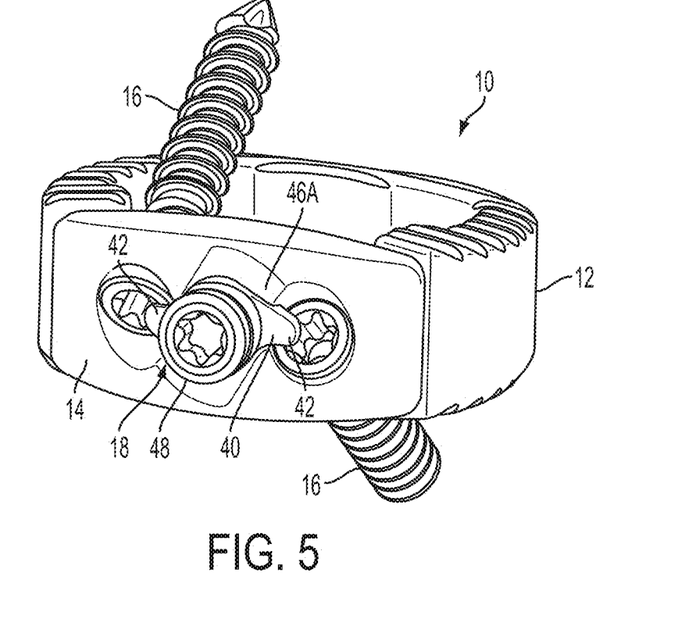
Figure 6:
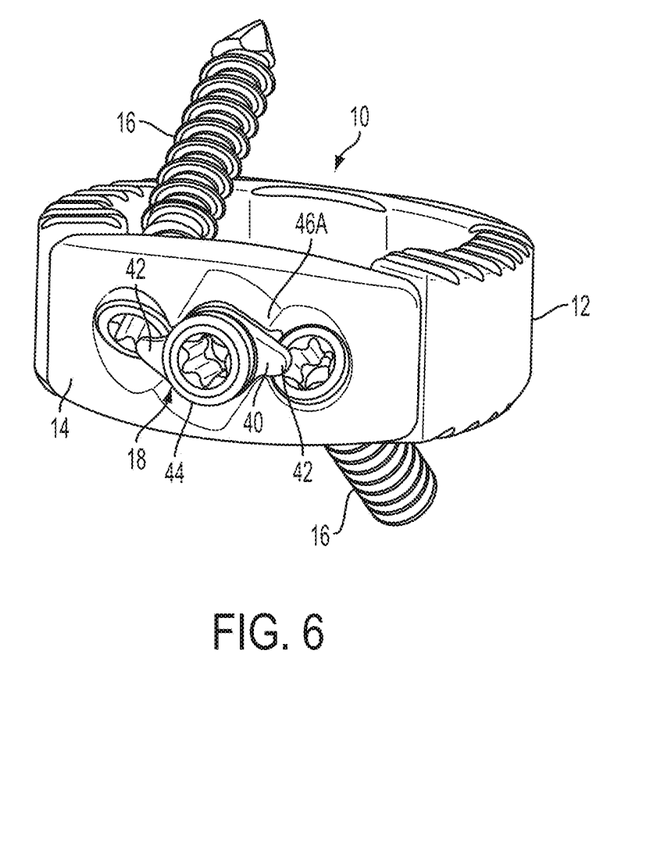

FIGS. 4-6 are isometric view illustrating the operation of the anti-backout mechanism described above. FIG. 4 shows the interbody fusion device 10 after the bone screws have been installed. Note that the position of the protrusions 42 of the locking plate 40 are such that the openings 34 are not obstructed, allowing a surgeon to install the bone screws 16. As mentioned above, the retention component 14 can come pre-assembled with the anti-backout mechanism 18 in the position shown in FIG. 4. Once the bone screws are in place, the surgeon can use a driver to turn the set screw 44 (see FIG. 6). FIG. 5 shows the interbody fusion device 10 after the set screw 44 has been turned. In this example, the set screw turned about 90 degrees until the protrusions 42 obstruct the heads of the bone screws 16. When the locking plate 40 is in this position, the bone screws cannot come out. As shown in FIGS. 4 and 5, the recess 46 has multiple depths. In this example, the recess has a first depth (shown at 46A) and a second deeper depth shown at 46B. As the locking plate 40 is turned, the locking plate will drop from the recess 46A and seat into the deeper recess 46B. When the locking plate 40 is seated within the deeper recess 46B (FIGS. 5 and 6), the shape of the recess 46 will tend to prevent the locking plate 40 from turning the other way. When the surgeon applies the appropriate amount of torque to the set screw 44, the head 48 of the set screw 44 will sheer off, eliminating the need for a torque wrench. This also lessens the profile of the implant. If the implant has to be removed in the future, a surgeon can use a driver and loosen the set screw 44 until the protrusions 42 no longer obstruct the bone screws 16.

Figure 7:
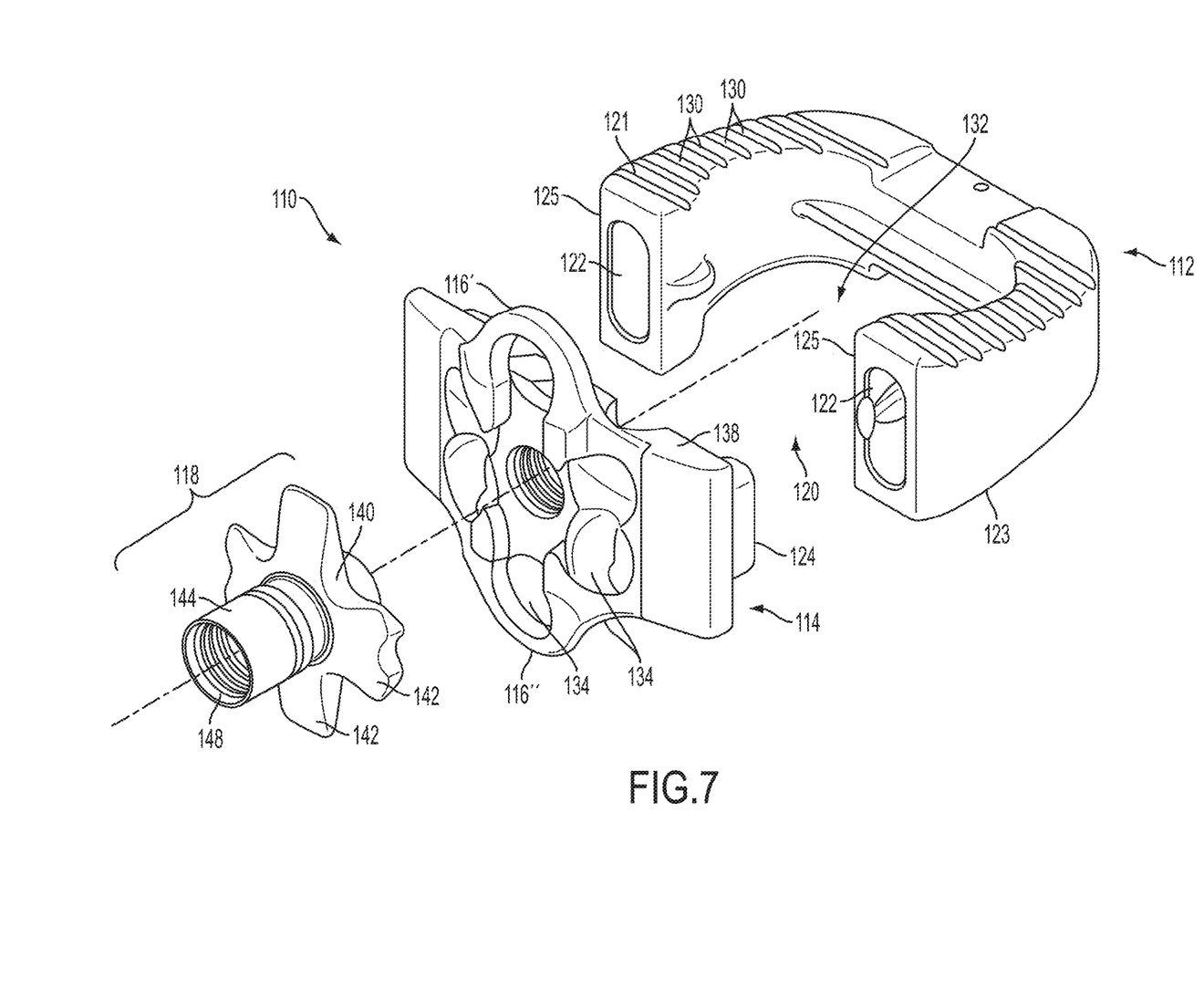
FIG. 7 is an anterior-lateral exploded isometric view of an illustrative example of a load-bearing interbody fusion device in accordance with an embodiment of the invention.
Figure 8:
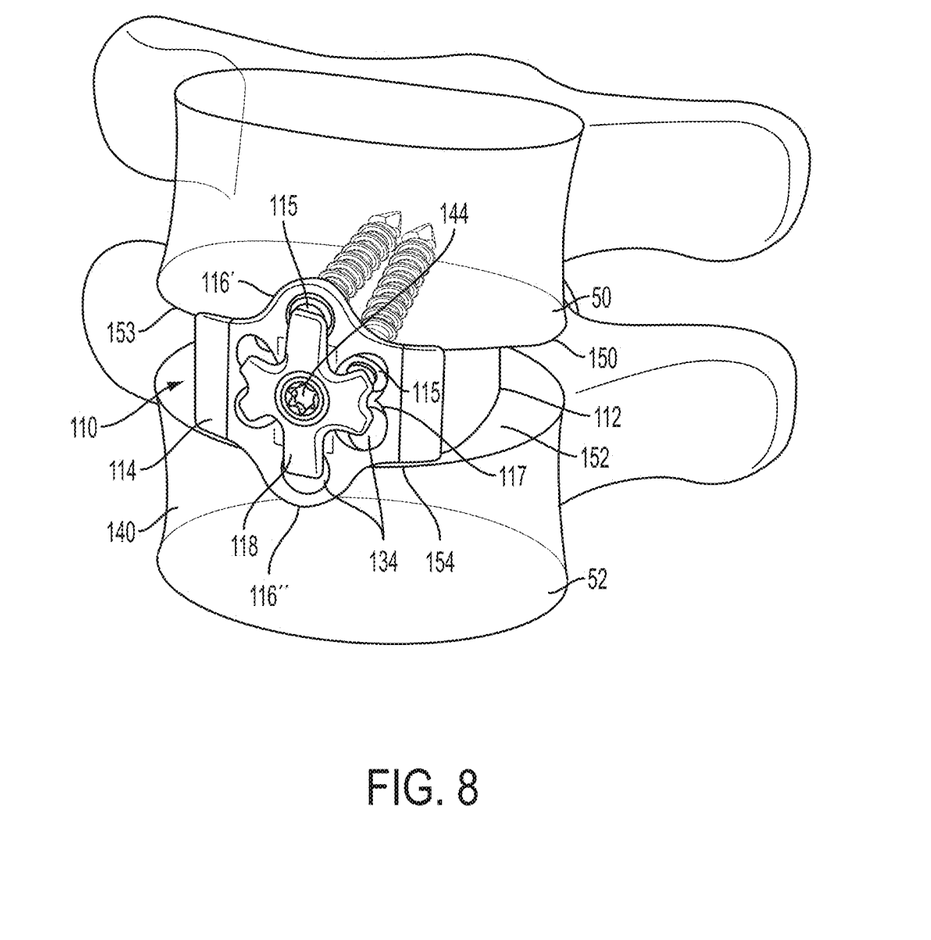
FIG. 8 is an isometric view of one example of an assembled load-bearing interbody fusion device in accordance with an embodiment of the invention.
Figure 9:
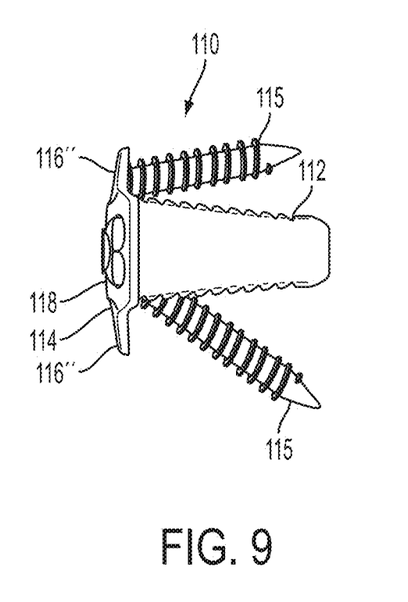
FIG. 9 is a side view of the load-bearing interbody fusion device in accordance with an embodiment of the invention.

Another embodiment of this invention is depicted in FIGS. 7-9, which are particularly adapted for fusion of L2-L5 and S1 and in particular L4/L5 and L5/S1, which create challenging access for the surgeon to place screws in the endplates. Due to sharper curve/angle of the vertebrae column, the spinal fusion device embodiment 110 shown in FIGS. 7-9 provide for multiple, constrained and/or non-constrained angles of entry for the fasteners, e.g., a 0 degree angle through 40 degrees on a challenging access retention component 114. This increased range of angles is provided by the lips 116', 116" and the various thru-bores 134 of the challenging access retention component 114, which abut the respective vertebrae's Apophyseal Rims. That is, the Apophyseal Rim approach allows for a decreased angle of the fasteners into the bone.

The embodiment of this invention 110 depicted in FIGS. 7-9 includes a fusion bearing component 112, a challenging access retention component 114, and from two to six fasteners 115. The challenging access retention component 114 has an upper lip 116' and lower lip 116", each having thru-bore 134, that abut the Apophyseal Rim during use and permit the fasteners 115 access to the anterior vertebral body to secure the spinal fusion device 110 into place. The face of the challenging access retention component 114 includes from two to four additional bores that permit the fasteners 115 access to the Apophyseal Rim to secure the spinal fusion device 110 into place. The challenging access retention component 114 also includes a threaded bore 136 configured for receipt of an anti-backout locking mechanism 118. The locking mechanism covers all screw bores in one motion when deployed.

FIG. 7 is an anterior-lateral exploded isometric view of another example of an interbody fusion device of the present invention. FIG. 7 shows an interbody fusion device 110. The interbody fusion device 110 includes a load bearing device 112. The load bearing device 112 also includes a plurality of ridges 130 formed on the top and bottom surfaces 121, 123 of the device 112. The ridges 130 are angled and come to a point in such a way that the ridges 130 help to hold the load bearing device 112 to the end plates of the vertebrae to reduce the chance of anterior migration of the implant. The load bearing device 112, also having recessed features 122 on the open-face ends 125 of the U-shaped body, configured to receive and capture mating attachment features 124 provided on a challenging access retention component with a minimalist anterior profile 114, and an anti-backout mechanism 118 comprising a shaped locking plate 140 having multiple protrusion or wings 142 and locking set screw 144 with a shear-off head 148, each of which are described in more detail below.

The challenging access retention component 114 and load bearing device 112, when put together to form an interbody fusion device 110, form a hollow body 132. The hollow body 132 provides a relatively large graft volume, compared to a typical ALIF allograft. After insertion of the load bearing device 112 between adjacent vertebrae, but before placement of the retention component 114, the endplates are debrided and prepared for fusion, and the hollow body 132 can be filled with a prepared material that will help to facilitate fusion of the vertebrae. Examples of a material include allograft bone, bone marrow, bone morphogenetic protein (BMP), Autologous Stem Cells, etc., to facilitate fusion through opening 132. Following placement of graft material, the challenging access device 114 is positioned and attached to the load-bearing fusion device. The retention component will maintain the graft material in place within the load-bearing fusion device, in addition to providing a compressive load to the load-bearing fusion device with the application of bone fasteners, such as bone screws inserted into the adjacent vertebrae.

In the example shown in FIG. 8, at least two holes 134 are formed in the retention component 114, and are adapted to receive fasteners, such as bone screws 115, pegs, etc. In the example shown in FIGS. 7 and 8, at least one of the holes 134 is angled down, and at least one other hole 34 is angled up, such that a first fastener 115 can be secured to the vertebra 50 above the interbody fusion device 110, and a second fastener 115 can be secured to the vertebra 52 below the interbody fusion device 110 (described in more detail below).

FIG. 8 is an isometric diagram of the interbody fusion device 110 shown in FIG. 7 installed between the end plates of two adjacent vertebrae 50 and 52 to facilitate the fusion of the vertebrae 50 and 52. The interbody fusion device 110 provides load bearing support as well as the proper spacing between the vertebrae 50 and 52 while fusion of the vertebrae takes place. As described in more detail below, the interbody fusion device 110 is positioned between the end plates of the vertebrae 50 and 52 within the vertebral body in the area usually occupied by the intervertebral disc. The load bearing device 112 is a generally U-shaped device having an open end (120 in FIG. 7) that is configured to receive a challenging access retention plate component 114. In the example shown in FIG. 7, a single opening is formed on the anterior side of the load bearing device 112. An implant holder can be used to insert the load bearing device 112 into a vertebral body using the openings 120.

The hollow U-shaped load bearing device 112 provides a relatively large graft volume, compared to a typical ALIF allograft. Prior to insertion of the challenging access retention component 114, the endplates of the vertebral bodies can be prepared for fusion as described in previous examples, then filled with a prepared material that will help to facilitate fusion of the vertebrae. Examples of a material include allograft bone, bone marrow, bone morphogenetic protein (BMP), Autologous Stem Cells, allogenic bone, growth factors and synthetic bone substitutes to facilitate fusion through opening 120.

Still referring to FIG. 8, a challenging access retention component 114 is provided with a anterior surface 117 and superior and inferior flanges 116' and 116", having a minimalist extended profile, symmetrically placed in the middle of the retention component, protruding above and below and anterior to the Apophyseal Rim 153 and 154 of each vertebra, above and below the load bearing device 110, each flange 116' and 116" having a thru-hole 134 to accommodate a fastener 115, such as a screw. Additionally the medial and lateral aspects of the challenging access retention component 114, approximately 50% of the anterior surface, are zero profile, not extending beyond the anterior plane of the vertebral bodies. Further, there are provided at least two thru-holes 134 to accommodate fasteners 115, such as bone screws that would allow penetration of the superior and inferior vertebral endplates 150 and 152 such that they would cause the vertebral bodies to compress the load-bearing interbody fusion device 112, thus promoting fusion. The challenging access retention component 114 is particularly useful when anatomic structures or general anatomy restrictions make it difficult for a surgeon to gain an adequate approach angle to properly deliver and tighten the fastener(s) 115 into one or more endplate(s) locations of the vertebrae. Hence providing alternate fixation locations such as the Apophyseal Rim 153 and 154, or anterior surface of the vertebra, just above the Apophyseal Rim. Clearance provided by any of the thru-bores 134 would be adequate to allow for constrained and/or non-constrained angulations of the screws 115. This would be desired to assure that the screws could be placed at any reasonable angle allowed by the constrained and/or non-constraining thru-bores 134, into the vertebral body 50, 52 or endplate(s) 150, 152, and also allow for eventual compressive settling of the vertebrae during fusion bone formation, without placing strain on the challenging access retention component 114 itself.

Still referring to FIG. 8, the challenging access retention component 114 is provided with an anti-backout mechanism 118 comprising a shaped locking plate 140 having multiple protrusion or wings 142 and locking set screw 144 with a shear-off head 148, configured to simultaneously cover all fastener thru-holes 134, wherein said shear-off head 148 is designed to shear off of the locking set screw 144, near flush to the surface of the challenging access retention component 114, when a pre-determined tightening torque is applied to the screw. The set screw in this example includes a driver socket for receiving a driver, which may be used by a surgeon to tighten the set screw 144. Of course, any desired type of anti-backout device may also be used.

FIG. 9 illustrates a side (lateral) view of the interbody fusion device 110, with the challenging access retention component 114, fasteners 115, and anti-backout locking mechanism 118, illustrating the minimalist dimensional features of the challenging access retention component 114 and flanges 116', 116", and angular insertion range of the fasteners 115 in various thru-bore positions. The dimensions shown are only illustrative and not intended to represent an upper or lower limit for sizing or angulations.

Figure 10A:
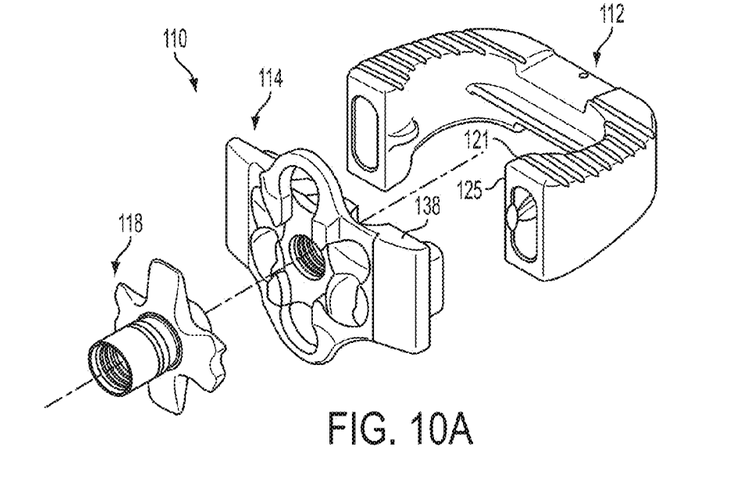
FIGS. 10A-10C are isometric diagrams of the interbody fusion device in accordance with an embodiment of the invention.
Figure 10B:
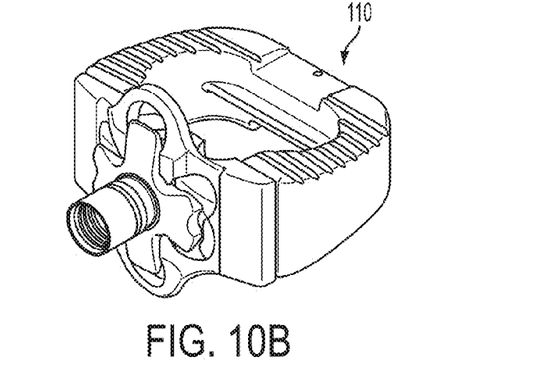
Figure 10C:
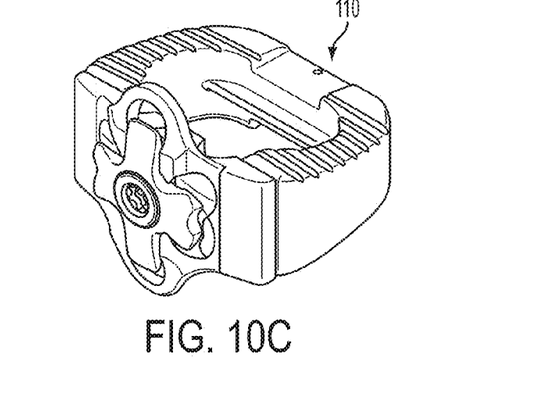

FIGS. 10A-10C are isometric diagrams of the illustrative interbody fusion device 110, comprising a load-bearing fusion device 112, the challenging access retention component 114 utilizing an anti-backout mechanism 118 in various stages between pre-assembly (FIG. 10A) and final assembly (FIG. 10C) (fasteners not shown, for clarity). As can be seen again in assemblies 10B and 10C, with the vertebral bodies removed, the superior surface of the challenging access retention component 138 (inferior surface 137—not shown) are equal to or less than the mating anterior height of the load-bearing fusion component 121 (inferior surface 123—not shown), at or about the location where the interbody fusion device assembly 110, or more specifically the superior and inferior surfaces of the assembled interbody fusion device 121, 123, 138, 137 near the interior face 135 of the challenging access retention component 114, would interface with the Apophyseal Rim 153, 154 and anterior aspects of the adjoining vertebral bodies 50, 52.

Figure 11:
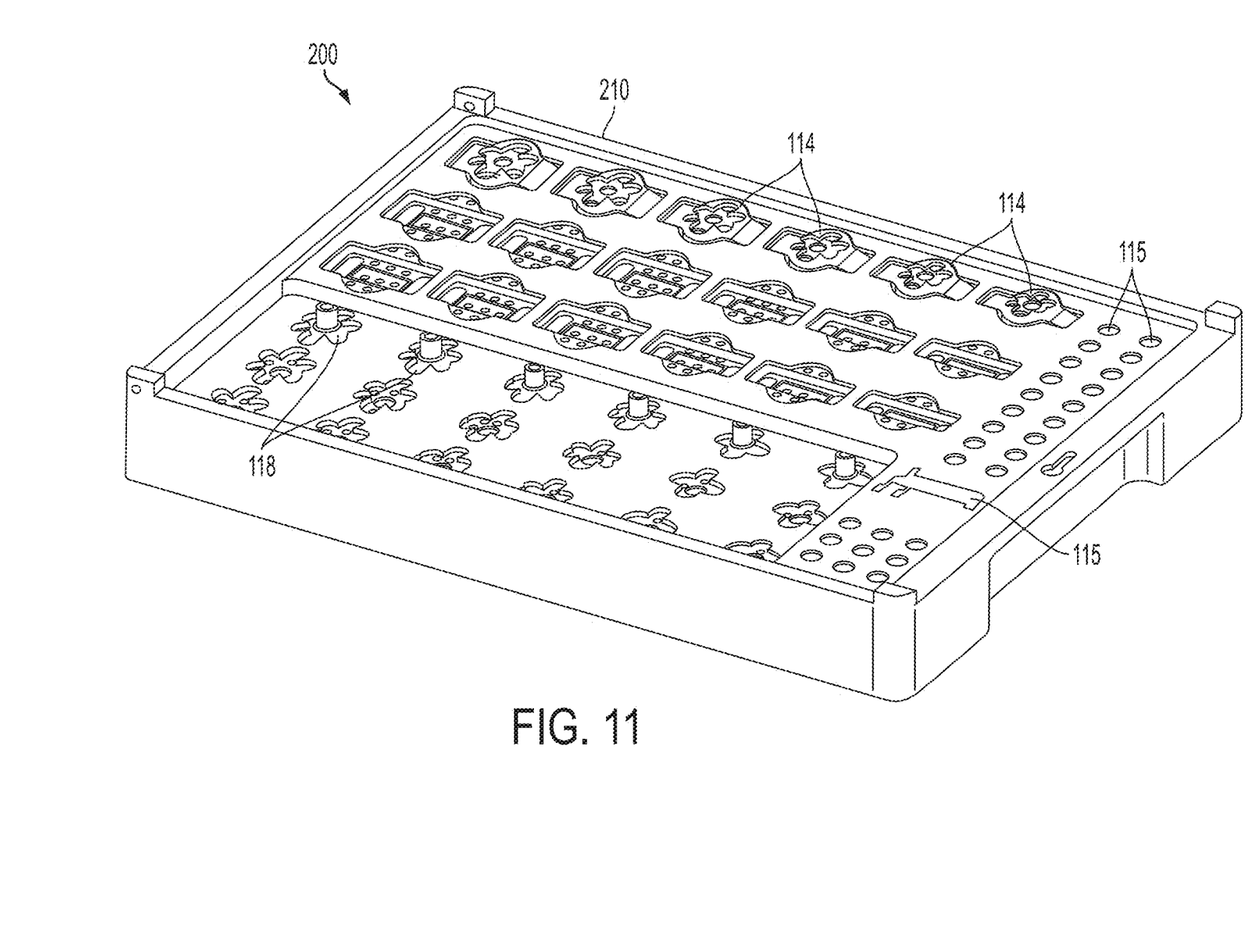
FIG. 11 is an isometric view of an illustrative kit in accordance with an embodiment of the invention.

FIG. 11 is an isometric view of an illustrative tray or caddy 210 to hold and present a Challenging Access Kit 200 for the various sizes and configurations of the challenging access retention components 114, various sizes and variations of anti-backout mechanisms 118, and available sizes and lengths of fasteners 115. (Load-bearing fusion devices 112, having multiple sizes, heights and/or widths and lordosis would be in a separate, but similar illustrative tray or caddy).

Each of the embodiments of the challenging access retention component has a low or minimal profile anteriorly. The locking mechanisms illustrated herein are not bound to any particular configuration and thus a given lock mechanism of a given embodiment in a FIG. 7 can be used in other embodiments.

Following is an example of how an interbody fusion device of the present invention may be used in an ALIF spinal fusion procedure. As described above, a window is cut in the anterior side of the disc annulus to allow an interbody fusion device to be inserted. Next, the nucleus pulposus is cleaned out to provide room for the interbody fusion device 110. Next, a load bearing component 112 of the desired size (e.g., having a height and lordosis necessary to achieve the desired spacing between the vertebrae) is inserted between the end plates of the adjacent vertebrae using the appropriate instrumentation. During these procedures, the endplates within the confines of the load bearing component are then scraped to promote a bleeding bed. A desired bone grafting material 54 is then placed in the hollow space 132 in the center of the load bearing fusion component 112. Once the surgeon is satisfied with placement of the graft material and that the load bearing component is in the ideal position, the challenging access retention component 114 is inserted and mated with the load bearing component 112. Note that, because the height of the challenging access retention component 114 is less than or equal to the height of the load bearing device, the challenging access retention component 114 can slide into the anterior vertebral space created by the load bearing component 112 without interfering with the relative placement of the load bearing component 112 and the end plates of the adjacent vertebrae 50, 52. Also, the challenging access retention component 114 is stress shielded and is not axial loaded by the vertebrae 50, 52. Once the challenging access retention component 114 is in place, the bone screws 115 can be installed through any of the thru-bore openings 134 and into the vertebrae 50, 52, preferably placing at least one fastener 115 into the cephalad vertebra 50, and a second fastener 115 into the caudal vertebra 52. As the bone screws 115 are tightened, they will compress vertebral bodies 50 and 52 onto the load bearing member 112, which will help facilitate fusion. Also, since the bone screws 115 secure the challenging access retention component 114, and do not directly secure the load bearing component 112, the bone screws will not tend to cause the assembled interbody fusion device 110 to migrate. If desired, an anti-backout mechanism 118 (such as that described in FIG. 7) can be used to prevent the bone screws 115 from loosening.

The interbody fusion device of the present invention can be made from any desired materials. In one example, the load bearing device is made from PEEK® (or a similar material), bone, metal, or any other structural substitute. In one example, the retention component is made from PEEK® (or a similar material), bone, metal, or any other structural substitute. If the components of the interbody fusion device are radio-lucent (such as with PEEK®), then doctors will be able to monitor the fusion process better with X-rays.

An interbody fusion device of the present invention may be configured to any desired size or shape. In one example, load bearing devices can be provided in multiple thicknesses, allowing a surgeon to select a desired size (e.g., 8.0 mm, 10.0 mm, 12.0 mm, 14.0 mm, etc.). In the examples shown in the figures, the load bearing device has about 5° of lordosis. However, any desired angle could be used.

In the preceding detailed description, the invention is described with reference to specific exemplary embodiments thereof and locations of use within the spine. Various modifications and changes may be made thereto without departing from the broader spirit and scope of the invention as set forth in the claims. The specification and drawings are, accordingly, to be regarded in an illustrative rather than a restrictive sense.

What is claimed is:

1. A spinal fusion device comprising:
an open-sided, generally U-shaped fusion bearing component configured to fit between two adjacent vertebrae and comprising two free ends; a separate, attachable symmetric retention component configured to be secured to the adjacent vertebrae to prevent migration of the fusion bearing component and loss of fusion material from the bearing component, wherein the retention component is configured to be non-load bearing and provide multiple apertures for fixation of fasteners into the endplates and/or the side wall of the adjacent vertebrae; an anti-backout mechanism to simultaneously prevent migration of the fasteners, wherein the anti-backout mechanism comprises a locking plate having one or more protrusions extending from the plate, wherein the one or more protrusions are configured to prevent migration of the fasteners when the locking plate is in the locked position and wherein each of the one or more protrusions contacts one of the fasteners when the locking plate is in the locked position; and a set screw for securing the locking plate in the locked position wherein the set screw includes a shear head coupled to the set screw and wherein the shear head is configured to break apart from the set screw when sufficient torque is applied to the shear head.

2. The spinal fusion device of claim 1, wherein the retention component is symmetric in the sagittal and transverse planes.

3. The spinal fusion device of claim 1, wherein the fasteners are bone screws.

4. The spinal fusion device of claim 1, wherein the retention component has a minimal profile superior and inferior flange for fastener fixation to the Apophyseal rim of the adjacent vertebrae.

5. The spinal fusion device of claim 1, wherein the retention component has a central minimal anterior profile not to exceed more than 3.5 mm beyond the anterior face of the adjacent vertebral bodies and at least 50% of the anterior profile is zero profile relative to the anterior face of the adjacent vertebral bodies.

6. The spinal fusion device of claim 1, wherein the medial half of the retention component is a mirror image of the lateral half of the retention component in the sagittal plane.

* * * * *